Figure 1:
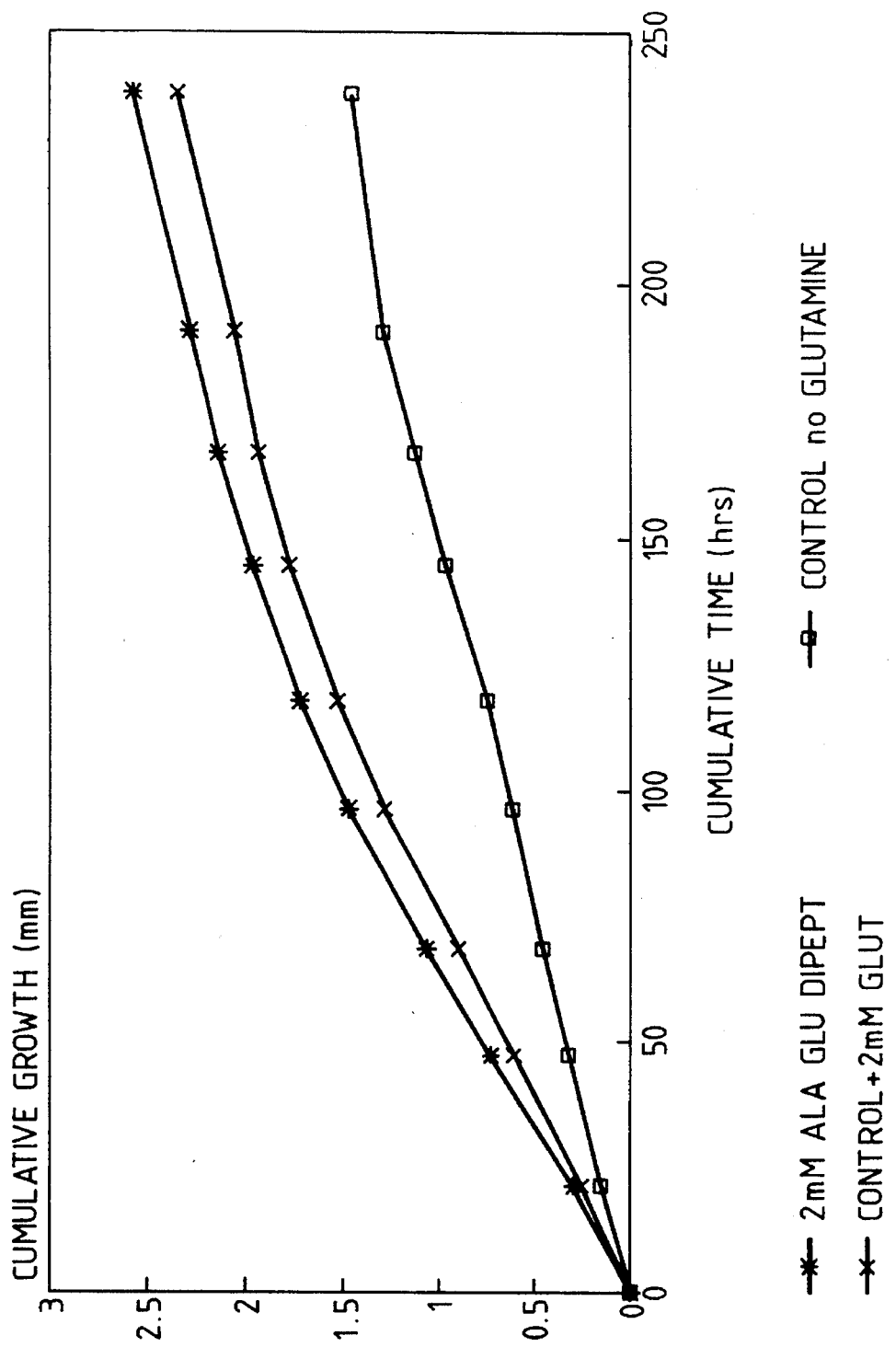

United States Patent [19]

Gibson et al.

[11] Patent Number: 5,559,092
[45] Date of Patent: Sep. 24, 1996

[54] COSMETIC COMPOSITION

[75] Inventors: Walter T. Gibson, Wellingborough; Gillian E. Westgate, Irthlingborough, both of United Kingdom

[73] Assignee: Chesebrough-Pond's USA Co. Division of Conopco, Inc., Greenwich, Conn.

[21] Appl. No.: 64,535

[22] Filed: May 19, 1993

[30]   Foreign Application Priority Data

May 20, 1992 [GB]   United Kingdom .................. 9210768

[51] Int. Cl.[6] .................................................. A61K 38/05
[52] U.S. Cl. .......................... 514/2; 132/202; 132/209; 424/70.1; 514/19; 514/881; 562/573
[58] Field of Search ................................ 562/573; 514/2, 514/19, 880, 881; 132/202, 209; 424/70.1

[56]   References Cited

U.S. PATENT DOCUMENTS

| | | | |
|---|---|---|---|
| 5,032,675 | 7/1991 | Kato et al. | 530/337 |
| 5,091,173 | 2/1992 | Buultjens et al. | 424/70 |

FOREIGN PATENT DOCUMENTS

| | | |
|---|---|---|
| 0415598 | 3/1991 | European Pat. Off. . |
| 0422765 | 4/1991 | European Pat. Off. . |
| 0490581 | 6/1992 | European Pat. Off. . |
| 1617477 | 6/1967 | Germany . |

OTHER PUBLICATIONS

Patent Abstracts of Japan vol. 11, No. 75 and JP-A 61 229 812, 1986.

Derwent Publication Ltd. and JP-A 62 027 499, 1987.

*Primary Examiner*—Shailendra Kumar
*Attorney, Agent, or Firm*—Milton L. Honig

[57]   ABSTRACT

A composition suitable for topical application to mammalian skin and hair for inducing, maintaining or increasing hair growth comprises a hair growth promoter chosen from glutamine derivatives and salts thereof. The composition preferably also comprises an activity enhancer which may be chosen from hair growth stimulants, penetration enhancers and cationic polymers.

12 Claims, 1 Drawing Sheet

COSMETIC COMPOSITION

FIELD OF THE INVENTION

The invention relates to cosmetic and pharmaceutical compositions for topical application to mammalian skin or hair, containing a hair growth promoter which is capable of increasing or maintaining hair growth, especially terminal hair growth on the human scalp.

BACKGROUND

The Hair Growth

It should be explained that in most mammals, hair does not grow continuously, but undergoes a cycle of activity involving alternate periods of growth and rest. The hair growth cycle can be divided into three main stages, namely:
(i) the growth phase known as anagen, during which the hair follicle penetrates deep into the dermis with the cells of the bulb dividing rapidly and differentiating to form the hair,
(ii) the transitional stage known as catagen, which is heralded by the cessation of mitosis, and during which the follicle regresses upwards through the dermis and hair growth ceases,
(iii) the resting stage known as telogen, in which the regressed follicle contains a small secondary germ with an underlying ball of tightly packed dermal papilla cells.

The initiation of a new anagen phase is revealed by rapid proliferation in the germ, expansion of the dermal papilla and elaboration of basement membrane components. The hair cycle is then repeated many times until, as a consequence of the onset of male pattern baldness, most of the hair follicles spend an increasing proportion of their time in the telogen stage, and the hairs produced become finer, shorter, and less visible; this is known as terminal to vellus transformation.

PRIOR ART

Alleged Baldness Cures

Although there have been many claims in the scientific literature to the promotion or maintenance of hair growth by the topical application of hair tonics and the like, with the possible exception of minoxidil, none has been shown to be sufficiently free from disadvantageous clinical side effects, whether administered topically, orally or systemically, to warrant commercial exploitation as an ethical pharmaceutical, proprietary medicine, or as a cosmetic product. Possibly, the only means which has met with partial success for growing hair on the bald or balding human head is by transplantation of hair to the bald areas. This is, however, an extremely painful operation and is not always successful. Furthermore, it is immediately apparent to the casual observer that the subject has received a hair transplant and it may take many months or even years before hair regrowth, following this operation, assumes an appearance which resembles that of the original naturally growing hair.

Among the many hair regrowth studies that have been reported in the literature, there is included the work of Bazzano as described in PCT International Publication No. WO 85/04577. This publication describes a composition which is useful for increasing the rates of hair growth on mammalian skin, prolonging the anagen phase of the hair growth cycle and for treating various types of alopecias. The composition in question comprises a pyrimidine carbamate.

It has also been reported in U.S. Pat. No. 4,139,619 to Chidsey assigned to the Upjohn Company, that a topical composition comprising minoxidil as the free base or acid addition salt thereof, or certain specified related iminopyrimidines, is useful in stimulating the conversion of vellus hair to growth as terminal hair, as well as increasing the rate of growth of terminal hair.

In spite of the apparent stimulation of hair growth or regrowth reported independently by Bazzano and Chidsey, following topical application of minoxidil or related compounds, there is general concern that systemic side-effects can result, particularly following topical application of minoxidil. Thus it is generally recognised in the medical literature that the side effects of orally administered minoxidil are very serious, and include fluid retention, tachycardia, dyspnea, gynecomastia, fatigue, nausea and cardiotoxicity. There is also evidence that certain side effects have been experienced following topical application of minoxidil.

It is also reported by Lion Corp., in JP 61151109 that compositions comprising mono-N-long chain acyl basic amino acid lower alkyl ester salt, together with higher fatty acid having an odd number of carbon atoms, higher aliphatic alcohol having an odd number of carbon atoms, or their derivatives, can be used for regenerating and growth increasing effect on hair.

Finally, DE 1617477 (Fischer) discloses a hair tonic which is said to guarantee hair growth. The tonic includes a variety of amino acids as well as four vitamins.

BACKGROUND TO THE INVENTION

Our own search for effective compositions that could be applied topically to the human scalp in order to promote hair growth, was influenced by the need to discover molecules which were not only effective but also completely safe in use and free from contra indications which would limit their appeal. Furthermore, we were anxious to identify relatively simple molecules in this respect which were easy to synthesis and inexpensive to deploy in a mass market affordable product which would appeal to a large number of potential consumers.

We have noted that the hair follicle has one of the highest rates of cell division in the body. This imposes considerable demands for energy to sustain rapid cell growth. Until recently, little was known of the preferred sources of energy for the hair follicle or the metabolic pathways by which they were utilised.

However, with the recent discovery of a method for maintaining follicle growth and hair production in vitro, we have been able for the first time to investigate the energy metabolism of hair follicles where we can be reasonably certain that experimental observations and conclusions will reflect the behaviour of follicles in vivo.

In the course of these experiements, we have found that the hair follicle can use, as a source of energy, several different fuels in addition to glucose. These include glutamine and certain derivatives of glutamine.

Surprisingly, we have found that these alternative fuels do not simply act as a replacement for glucose in terms of energy production. Even in the presence of glucose, we have observed that significant stimulation of linear hair growth rate can be obtained by supplying small amounts of one or more of them.

Having established from in vitro studies using isolated human follicles that glutamine is a potent promoter of linear hair growth, it was subsequently discovered that glutamine tends to be unstable when formulated in an aqueous hair treatment composition such as a shampoo, conditioner or tonic. It was thus observed that after storage in such compositions at an ambient temperature for 3 months, a significant amount of the glutamine had been converted to pyroglutamic acid and ammonia. From these observations, it was realised that the αNH$_2$ group of glutamine should be protected in order to stabilise the molecule.

Further investigations showed that acylation or formation of a peptide through the αNH$_2$ group of glutamine yielded acyl glutamines or glutamine peptides that were not only stable during storage in aqueous hair treatment products, but also possessed activity equivalent to that of freshly prepared glutamine—containing compositions in the stimulation of linear hair growth. It was also noted that certain of these derivatives offer further advantages in use, in that they exhibit improved penetration through the skin and enhance delivery to the hair follicle, when compared with glutamine itself.

The invention is accordingly concerned with the promotion of hair growth using special glutamine derivatives.

DEFINITION OF THE INVENTION

Accordingly, the invention provides a composition suitable for topical application to mammalian skin or hair for inducing, maintaining or increasing hair growth, which comprises:

i. an effective amount of from 0.001 to 99% by weight of a hair growth promoter chosen from glutamine derivatives having the structure (1):

where $R^1$ is chosen from:
 (i) H—,
 (ii) $C_xH_y$—, and
 (iii) $C_xH_yCO$—;
and where $R^2$ is chosen from:
 (i) H—,
 (ii) $C_xH_y$—, and
 (iii) $C_xH_yCO$—;
 (iv) amino acid residues, or substituted amino acid residues where any free —NH$_2$ group is modified to form a —NHCOC$_x$H$_y$ or a —NHC$_x$H$_y$ group, and/or any free -COOH group is substituted to form a COOR$^3$ group,
 (v) peptide residues comprising from 2 to 8 amino acid residues or substituted amino acid residues, which are substituted as defined in (iv) above;
the amino acid residues or substituted amino acid residues, as herein defined, being derived from one or more of the following amino acids:
 L- α-alanine
 L- β-alanine
 L- arginine
 L- γ- amino butyric acid
 L- asparagine
 L- aspartic acid
 L- citrulline
 L- cysteine
 L- cystine
 L- 3,4-dihydroxyphenylalanine (DOPA)
 L- glutamine
 L- glutamic acid
 L- glycine
 L- histidine
 L- homoserine
 L- hydroxylysine
 L- hydroxyproline
 L- isoleucine
 L- leucine
 L- lysine
 L- methionine
 L- ornithine
 L- phenylalanine
 L- proline
 L- serine
 L- threonine
 L- N,N,N-trimethyl glycine (betaine)
 L- tryptophan
 L- tyrosine, and
 L- valine;
and where $R^3$ is chosen from:
 (i) H$^+$,
 (ii) alkali metal cations chosen from Na$^+$, K$^+$ and Li$^+$,
 (iii) NH$_4^+$ or alkanolammonium ions, and
 (iv) C$_x$H$_y$—;
where
 x is a integer of from 1 to 22 and
 y is an integer of from 3 to 45;
provided that when $R^1$ and $R^2$ are both -H, then $R^3$ is C$_x$H$_y$—; and mixtures of said glutamine derivatives;

ii. from 1 to 99.99% by weight of a cosmetically acceptable vehicle for the hair growth promoter.

DISCLOSURE OF THE INVENTION

The Hair Growth Promoter

According to the invention, the composition comprises a hair growth promoter chosen from glutamine derivatives having the structure (1).

Preferred examples of glutamine derivatives where the group. $R^2$ is an amino acid residue are the dipeptides:
 L- α-alanylglutamine (2)
 L- β-alanylglutamine (3)
 L- asparaginylglutamine (4)
 L- citrulinylglutamine (5)
 L- cysteinylglutamine (6)
 L- 3,4-dihydroxyphenylalanylglutamine (7)
 L- cystinylglutamine (8)
 L- glutaminylglutamine (9)
 L- glutamylglutamine (10)
 L- methionylglutamine, (11), and
 L- tyrosinylglutamine (12);
and their corresponding sodium or potassium salts.

Preferred examples of glutamine derivatives where the group $R^2$ is a peptide residue are the tripeptides.
 L- α-alanylmethionylglutamine (13)
 L- β-alanylcysteinylglutamine (14)
 L- methionylglutaminylglutamine (15), and
 L- citrulinylglutamylglutamine (16);
and their corresponding sodium or potassium salts.

Preferred examples of glutamine derivatives where the group $R^2$ is an acyl group are:

N- propanoylglutamine (17)
N- butanoylglutamine (18)
N- hexanoylglutamine (19)
N- octanoylglutamine (20)
N- nonanoylglutamine (21)
N- decanoylglutamine (22)
N- undecanoylglutamine (23)
N- dodecanoylglutamine (24)
N- tetradecanoylglutamine (25)
N- hexadecanoylglutamine (26)
N- octadecanoylglutamine (27), and
N- eicosanoylglutamine (28).

Preferred examples of glutamine derivatives where the group $R^3$ is an alkyl group are:
methylglutamine (29)
ethylglutamine (30)
n- propylglutamine (31)
iso-propylglutamine (32)
n- butylglutamine (33)
n- hexylglutamine (34)
n- octylglutamine (35)
n- nonylglutamine (36)
n- decylglutamine (37)
n-dodecylglutamine (38)
n- tetradecylglutamine (39)
n- hexadecylglutamine (40), and
n- octadecylglutamine (41)
and their corresponding sodium or potassium salt.

Selected glutamine derivatives from those given above and identified by numbers (2) to (41) are further illustrated in the Examples given hereinafter, where they are identified as "Promoter" with the relevant number in parenthesis.

A particularly preferred example of a glutamine derivative is the dipeptide α-alanyl glutamine (α-Ala-Gln) having the structure (1a):

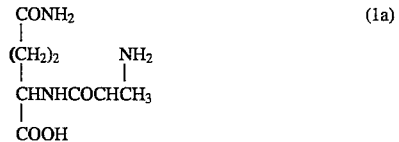

or the sodium salt thereof, where M in structure (1) is Na.

The composition can comprise two more hair growth promoters, as herein defined.

The total amount of the hair growth promoter present in the composition according to the invention is an amount which is sufficient to induce maintain or increase hair growth. This amount will depend on the effectiveness of the promoter, Some being more effective than others, but in general an amount of from 0.001 to 99%, usually from 0.01 to 20% by weight of the composition will provide an adequate concentration for application to the skin, particularly the scalp, which can then be repeated as necessary to promote hair growth.

The Cosmetically Acceptable Vehicle

The composition according to the invention also comprises a solid, semi-solid or liquid cosmetically and/or physiologically acceptable vehicle, to enable the hair growth promoter to be conveyed to the skin at an appropriate dilution. The nature of the vehicle will depend upon the method chosen for topical administration of the composition. The vehicle can itself be inert or it can possess physiological or pharmaceutical benefits of its own.

The selection of a vehicle for this purpose presents a wide range of possibilities depending on the required product form of the composition. Suitable vehicles can be classified as described hereinafter.

It should be explained that vehicles are substances which can act as diluents, dispersants, or solvents for the hair growth promoter which therefore ensure that they can be applied to and distributed evenly over the hair and/or scalp at an appropriate concentration. The vehicle is preferably one which can aid penetration of the esters into the skin to reach the immediate environment of the hair follicle. Compositions according to this invention can include water as a vehicle, and/or at least one cosmetically acceptable vehicle other than water.

Vehicles other than water that can be used in compositions according to the invention can include solids or liquids such as emollients, solvents, humectants, thickeners and powders. Examples of each of these types of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, mink oil, cetyl alcohol, ispropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polythylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as propane, butane, isobutane, dimethyl ether, carbon dioxide, nitrous oxide;

Solvents, such as ethyl alcohol, methylene chloride, isopropanol, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The amount of vehicle in the composition, including water if present, should preferably be sufficient to carry at least a portion of a selected hair growth promoter to the skin in an amount which is sufficient effectively to enhance hair growth. The amount of the vehicle can comprise the balance of the composition, particularly where little or no other ingredients are present in the composition. Accordingly, the vehicle or vehicles can comprise from 1 to 99.99%, preferably from 50 to 99.5% and ideally from 90 to 99% by weight of the composition.

Perfume

The composition according to the invention can also optionally comprise a perfume in an amount sufficient to make the composition acceptable to the consumer and pleasant to use. Usually, the perfume will form from 0.01 to 10% by weight of the composition.

Activity Enhancer

The composition according to the invention can also optionally comprise an activity enhancer.

The activity enhancer can be chosen from a wide variety of molecules which can function in different ways to enhance the hair growth effects of the hair growth promoter. Particular classes of activity enhancers include (a) other hair growth stimulants, (b) penetration enhancers and (c) cationic polymers, whose presence can further improve the delivery of the ester through the stratum corneum to its site of action in the immediate environment of the hair follicle.

Some activity enhancers can also function as vehicles for the ester.

(a) Other Hair Growth Stimulants i. Examples of other substances which themselves possess the ability to stimulate or increase hair growth include, for example:

Benzalkonium chloride
Benzethonium chloride
Phenol
Estradiol
Diphenhydramine hydrochloride
Chlorpheniramine maleate
Chlorophyllin derivatives
Cholesterol
Salicylic acid
Cystine
Methionine
Red pepper tincture
Benzyl nicotinate
dl-Menthol
Peppermint oil
Calcium pantothenate
Panthenol
Castor oil
Hinokitiol
Prednisolone
Resorcinol Further substances which themselves possess the ability to increase the rate of terminal hair growth include:

ii. α-1,4 esterified disaccharides described by Choay S. A. in EP-A-O 064 012, having the structure (3):

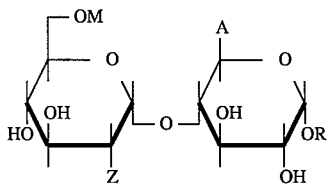

where

Z represents a functional nitrogen group, such as an azide or a group having the structure -NHB, in which B represents -H or a functional group such as acetyl or sulphate as a salt with an organic or mineral cation;

M represents —H or $SO_3M_1$, where $M_1$ is an organic or metallic cation, particularly an alkali metal; or an acetyl group;

R represents a $C_1$ to $C_4$ alkyl radical, especially methyl; or an aryl radical;

A represents a functional group such as an acid or —$COOR_1$, where $R_1$ represents —H or a $C_1$ to $C_4$ alkyl radical, especially methyl; or a metal, especially an alkali metal;

esterified oligosaccharides as described by Unilever in EP-A-O 211 610, including at least one esterified disaccharide unit consisting of a uronic acid residue having the structure (4):

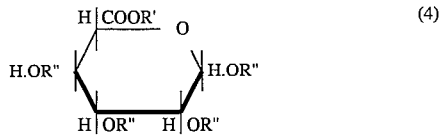

and a hexosamine residue having the structure (5):

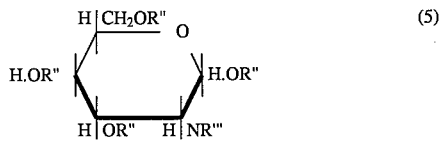

where

R' is —H $C_3$ to $C_{10}$ alkyl or

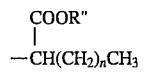

R" is —H, $C_1$ to $C_4$ alkyl, —$CO(CH_2)_mCH_3$, —$SO_3M$,
R'" is —H, —$CO(CH_2)_mCH_3$, or —$SO_3M$,
M is —H, or a metallic or organic cation
n is 0 or an integer of from 1 to 7, and m is 0 or the integer 1 or 2;
the groups designated R" being the same or different, one R" group from each pyranose ring structure being linked by a glycosidic linkage having the configuration α-1,3, α-1,4, β-1,3 or β-1,4; and the —COOR', —$CH_2OR$" and —OR" groups being of either configuration with respect to the pyranose rings;

iii. Minoxidil glucuronides, as described by Unilever in EP-0 242 967, iv. Minoxidil sulphates, as described by The Upjohn Co. in WO 86/04231, and v. Minoxidil, and other derivatives thereof as described by The Upjohn Co, in U.S. Pat. No. 4,139,619.

A particularly preferred mixture of minoxidil and a hair growth promoter according to the invention is minoxidil and α-alanylglutamine.

vi. Ethylenediaminetetraacetic acid or salts thereof, as described by Redken Laboratories, Inc. in U.S. Pat. No. 4,814,351.

vii. Direct proteoglycanase inhibitors, such as 1,10-phenanthroline, as described by Unilever in EP-0 277 428.

viii. Glycosaminoglycanase inhibitors, as described by Unilever in EP-0 277 428, such as aldonolactones and esterified aldonolactones, preferred examples of which include:
L-Galactono-1,4-lactone
L-Arabino-1,5-lactone
D-Fucono-1,5-lactone
D-Glucaro-1,4-lactone
D-Glucurono-6,3-lactone
Galactaric acid lactone
2-Acetamido-2-deoxygluconolactone
2-Acetamido-2-deoxygalactono-lactone
D-Glucaro-1,4:6,3-dilactone
L-Idaro-1,4-lactone
2,3,5-Tri-0-acetyl-D-glucaro-1,4-lactone
2,5-Di-0-acetyl-D-glucaro-1,4:6,3-dilactone.

ix. Glycosaminoglycanase inhibitors, as described by Unilever in EP 0 277 428, such as monosaccharides and esterified monosaccharides, preferred examples of which include:
N-Acetylglucosamine N-Acetylgalactosamine
D-Galactosamine
D-Glucosamine-3-sulphate
N-Acetylmannosamine.

x. Glycosaminoglycan chain cellular uptake inhibitors, as described by Unilever in EP 0 277 428, such as hexuronic acid and esters thereof.

xi. Chemical inhibitors of glycosidase activity, as described by Unilever in EP 0 334 586, chosen from lactams,
preferred examples of which include:
D-glucaro-1,5-lactam,
L-Galactono-1,4-lactam,
L-Arabino-1,5-lactam,
D-Fucono-1,5-lactam,
D-Glucaro-1,4-lactam,
D-Glucurono-6,3-lactam,
1,2,5-tri-O-acetyl-D-glucurono-6,3-lactam,
2-Acetamido-2-deoxygluconolactam,
2-Acetamido-2-deoxygalactonolactam,
D-Glucaro-1,4:6,3-dilactam,
L-Idaro-1,4-lactam,
2,3,5-Tri-O-acetyl-D-glucaro-1,4-lactam,
2,5-Di-O-acetyl-D-Glucaro-1,4:6,3-dilactam,
D-glucaro-1,5-lactam ethyl ester;

xii. Chemical activators of protein kinase C enzymes, as described by Unilever in EP 0 334 585 chosen from diacylglycerols,
preferred examples of which include:
1,2-Dibutanoyl-rac-glycerol
1,2-Dihexanoyl-sn-glycerol
1,2-Dioctanoyl-rac-glycerol
1,2-Dioctanoyl-sn-glycerol
1,2-Didecanoyl-rac-glycerol
1-Oleoyl-2-acetyl-rac-glycerol
1-Oleoyl-2-acetyl-sn-glycerol
1-Stearoyl-2-arachidonoyl-sn-glycerol
1,2-Distearoyl-rac-glycerol
1,2-Dipentadecanoyl-sn-glycerol
1,2-dipentadecanoyl-rac-glycerol
1,2-Dipalmitoyl-rac-glycerol
1,2-Dipalmitoyl-sn-glycerol
1,2-Diseptadecanoyl-rac-glycerol
1,2-Dioleoyl-sn-glycerol
1,2-Dioleoyl-rac-glycerol
1,2-Diarachidonoyl-sn-glycerol
1,2-Dieicosanoyl-sn-glycerol
1,2-Didoeicosanoyl-rac-glycerol, and
1,2-Dioctaeicosanoyl-sn-glycerol.

xiii. Glycosaminoglycanase inhibitors, as described by Unilever in EP 0 348 184, chosen from aldonomonolactone or alduronomonolactone derivatives,
preferred examples of which aldonomonolactone derivatives include:
6-acetyl-galactono-1,4-lactone
6-propionyl-galactono-1,4-lactone
6-butyryl-galactono-1,4-lactone
2-propionamido-2-deoxygluconolactone
2-butyramido-2-deoxygluconolactone
2-propionamido-2-deoxygalactonolactone
2-butyramido-2-deoxygalactonolactone
6-propionyl-2-acetamido-2-deoxygluconolactone
diacetyl-6-propionyl-2-acetamido-2-deoxygluconolactone
6-butyryl-2-acetamido-2-deoxygalactonolactone
diacetyl-6-butyryl-2-acetamido-2-deoxygalactonolactone
2,3,5,6-tetraacetyl-galactono-1,4-lactone
2,3,5-triacetyl-6-propionylgalactono-1,4-lactone
triacetyl-2-propionamido-2-deoxygalactonolactone
triacetyl-2-butyramido-2-deoxygluconolactone
6-methyl-glucaro-1,4-lactone
2,3,5,6-tetramethyl-glucaro-1,4-lactone
6-methyl-2,3,5-triacetylglucaro-1,4-lactone
6-methyl-3-methyl-glucaro-1,4-lactone, and
6-methyl-3-acetyl-glucaro-1,4-lactone;
and a preferred example of which alduronomonolactone derivative is:
1,2,5-triacetyl-glucurono-6,3-lactone.

xiv. Glycosaminoglycanase inhibitors, as described by Unilever in EP 0 348 184, chosen from acylated monosaccharides,
preferred examples of which acylated monosaccharides include:
2-propionamido-2-deoxyglucose
1,3,4,6-tetraacetyl-2-propionamido-2-deoxyglucose
2-butyramido-2-deoxygalactose
1,3,4,6-tetraacetyl-2-butyramido-2-deoxygalactose
2-sulphamido-2-deoxygalactose
2-sulphamido-2-deoxyglucose
2-butyramido-2-deoxymannose
1,3,4,6-tetraacetyl-2-butyramido-2-deoxymannose
2-butyramido-2-deoxyglucose, and
1,3,4,6-tetraacetyl-2-butyramido-2-deoxyglucose.

xv. Esters of pyroglutamic acid, as described by Lever Brothers Company in U.S. Pat. No. 4,774,255,
preferred examples of which include:
pyroglutamic acid methyl ester
pyroglutamic acid ethyl ester
pyroglutamic acid n-propyl ester
pyroglutamic acid n-butyl ester
pyroglutamic acid n-hexyl ester
pyroglutamic acid n-heptyl ester
pyroglutamic acid n-octyl ester
pyroglutamic acid n-nonyl ester
pyroglutamic acid n-decyl ester
pyroglutamic acid n-undecyl ester
pyroglutamic acid n-dodecyl ester
pyroglutamic acid n-tridecyl ester
pyroglutamic acid n-tetradcyl ester
pyroglutamic acid n-hexadecyl ester
pyroglutamic acid n-octadecyl ester
pyroglutamic acid n-eicosyl ester
pyroglutamic acid iso-propyl ester
pyroglutamic acid 2-methylhexyl ester
pyroglutamic acid 2-ethylhexyl ester
pyroglutamic acid 3,7-dimethyloctyl ester
pyroglutamic acid 2-hexyldecyl ester
pyroglutamic acid 2-octyldodecyl ester
pyroglutamic acid 2,4,4-trimetyl-1-pentane ester
pyroglutamic acid methyloctyl ester
2-[pyroglutamoyloxy]-propionic acid
methyl-2-[pyroglutamoyloxy]-acetate
ethyl-2-[pyroglutamoyloxy]-n-propionate
ethyl-2-[pyroglutamoyloxy]-n-butyrate
ethyl-2-[pyroglutamoyloxy]-iso-butyrate
ethyl-2-[pyroglutamoyloxy]-n-valerate
ethyl-2-[pyroglutamoyloxy]-n-caproate
ethyl-2-[pyroglutamoyloxy]-n-heptylate
ethyl-2-[pyroglutamoyloxy]-n-caprylate
ethyl-2-[pyroglutamoyloxy]-n-pelargonate
ethyl-2-[pyroglutamoyloxy]-3-hydroxybutyrate
iso-propyl-2-[pyroglutamoyloxy]-n-propionate
iso-propyl-2-[pyroglutamoyloxy]-n-caprylate
n-propyl-2-[pyroglutamoyloxy]-n-propionate
n-propyl-2-[pyroglutamoyloxy]-n-caprylate stearyl-2-[pyroglutamoyloxy]-n-propionate
12-hydroxystearyl-2-[pyroglutamoyloxy]-n-propionate
stearyl-2-[pyroglutamoyloxy]-n-stearate
palmityl -2-[pyroglutamoyloxy]-n-propionate
linoleyl -2-[pyroglutamoyloxy]-n-propionate
linoleyl -2-[pyroglutamoyloxy]-n-caprylate
lauryl-2 -[pyroglutamoyloxy]-n-caprylate
stearyl- 2-[pyroglutamoyloxy]-n-caprylate
glyceryl mono(2-[pyroglutamoyloxy]-n-propionate)
glyceryl mono(2-[pyroglutamoyloxy]-n-caprylate), and
glyceryl di(2-[pyroglutamoyloxy]-n-propionate).

xvi. hexosaccharic acids or an acylated hexosaccharic acids, or salts or esters thereof, as described by Unilever in EP 378 388 preferred examples of which include:
allosaccharic acid
altrosaccharic acid
glucosaccharic acid
mannosaccharic acid
gulosaccharic acid
idosaccharic acid
galactosaccharic acid
talosaccharic acid, and
their disodium salts.

xvii. aryl-substituted ethylenes as described by Unilever in EP 403 238, preferred examples of which include:
1-carboxy-2-(4-hydroxyphenyl)ethylene
1,1-dicarboxy-2-(4-hydroxyphenyl)ethylene
1,1-dicyano-2-(4-hydroxyphenyl)ethylene
1-carboxy-2-(3,4-dihydroxyphenyl)ethylene
1,1-dicyano-2-(3-hydroxyphenyl)ethylene
1-cyano-1-carboxy-2-(2,5-dihydroxyphenyl)ethylene
1-carboxy-1-cyano-2-(3,4-dihydroxphenyl)ethylene
1,1-dicyano-2-(3,4-dihydroxyphenyl)ethylene
1,1-dicyano-2-(3-methoxy-4,5-dihydroxyphenyl)ethylene
1,1-dicyano-2-(3,4,5-trihydroxyphenyl)ethylene
1-amido-1-cyano-2-(3,4-dihydroxyphenyl)ethylene
1-thioamido-1-cyano-2-(3,4-dihydroxyphenyl)ethylene
1-cyano-2-(4-hydroxyphenyl)ethylene
1,1-dicyano-2-(3-hydroxy-4-nitrophenyl)ethylene
1,1-dicyano-2-hydroxy-2-(4-hydroxyphenyl)ethylene
1,1-dicyano-2-(3-methoxy-4-hydroxyphenyl)ethylene
1,1-dicyano-2-(3,5-dihydroxyphenyl)ethylene
1,1-dicyano-2-hydroxy-2-(3,4,5-trihydroxyphenyl)ethylene
1-carboxy-1-cyano-2-(4-methoxyphenyl)ethylene
1-carboxy-1-cyano-2-(4-fluorophenyl)ethylene
1-carboxy-1-cyano-2-(3-methoxy-4-hydroxyphenyl)ethylene
1-carboxy-1-cyano-2-(3,5-dimethoxy-4-hydroxyphenyl)ethylene
1-carboxy-1-cyano-2-(4-hydroxyphenyl)ethylene
1-carboxy-1-cyano-2-(4-phenylcarboxyaldehyde)ethylene, and
1-cyano-1-carboxy-2-(2,5-dihydroxyphenyl)ethylene xviii. N-acylated amino acids as described by Unilever in EP 415 598.

Preferred examples of which include:
N-acetyl glycine
N-acetyl hydroxyproline
N-acetyl alanine
N-acetyl valine
N-acetyl leucine
N-acetyl isoleucine
N-acetyl phenylalanine
N-acetyl tyrosine
N-acetyl proline
N-acetyl serine
N-acetyl threonine
N-acetyl cysteine
N-acetyl cystine
N-acetyl methionine
N-acetyl tryptophan
N-lauroyl glycine
N-palmitoyl glycine
N-myristoyl glycine
N-lauroyl hydroxyproline
N-octanoyl glycine
N-octanoyl hydroxyproline
N-hexanoyl glycine
N-acetyl aspartic acid
N-lauroyl aspartic acid
N-palmitoyl aspartic acid
N-octanoyl aspartic acid
N-acetyl glutamic acid
N-lauroyl glutamic acid
N-palmitoyl glutamic acid
N-octanoyl glutamic acid
N-acetyl arginine
N-acetyl lysine
N-acetyl histidine
N-acetyl ornithine
N-acetyl hydroxylysine
N-acetyl citrulline
N-lauroyl lysine
N-lauroyl citrulline
N-myristoyl citrulline
N-myristoyl ornithine
N-octanoyl lysine, and
N-octanoyl citrulline.

(b) Penetration Enhancers

As has been stated earlier, the presence of a penetration enhancer can potentiate the benefit of the hair growth promoter by improving its delivery through the stratum corneum to its site of action in the immediate environment of the hair follicle close to the dermal papilla.

The penetration enhancer can accordingly function in a variety of ways. It can for example, improve the distribution of the hair growth promoter on the skin surface or, it can increase its partition into the skin from the composition when applied topically, so aiding its passage to its site of action. Other mechanisms enhancing the benefit of the hair growth promoter may also be involved.

Examples of penetration enhancers include:
2-methyl propan-2-ol
Propan-2-ol
Ethyl-2-hydroxypropanoate
Hexan-2,5-diol
POE(2) ethyl ether
Di(2-hydroxypropyl) ether
Pentan-2,4-diol
Acetone
POE(2) methyl ether
2-hydroxypropionic acid
2-hydroxyoctanoic acid
Propan-1-ol
1,4 Dioxane
Tetrahydrofuran
Butan-1,4-diol
Propylene glycol dipelargonate
Polyoxypropylene 15 stearyl ether
Octyl alcohol POE ester of oleyl alcohol
Oleyl alcohol
Lauryl alcohol
Dioctyl adipate
Dicapryl adipate
Diisopropyl adipate
Diisopropyl sebacate
Dibutyl sebacate
Diethyl sebacate
Dimethyl sebacate
Dioctyl sebacate
Dibutyl suberate
Dioctyl azelate
Debenzyl sebacate
Dibutyl phthalate
Dibutyl azelate
Ethyl myristate
Dimethyl azelate
Butyl myristate
Dibutyl succinate
Didecyl phthalate
Decyl oleate
Ethyl caproate
Ethyl salicylate
Isopropyl palmitate
Ethyl laurate
2-ethyl-hexyl pelargonate
Isopropyl isostearate
Butyl laurate
Benzyl benzoate
Butyl benzoate
Hexyl laurate
Ethyl caprate
Ethyl caprylate
Butyl stearate
Benzyl salicylate
2-hydroxypropanoic acid
2-hyroxyoctanoic acid,
Dimethyl sulphoxide
N,N-Dimethyl acetamide
N,N-Dimethyl formamide
2-Pyrrolidone
1-Methyl-2-pyrrolidone
5-Methyl-2-pyrrolidone
1,5-Dimethyl-2-pyrrolidone
1-Ethyl-2-pyrrolidone
Phosphine oxides
Sugar esters
Tetrahydrofurfural alcohol
Urea
Diethyl-m-toluamide, and
1-Dodecylazacyloheptan-2-one
(c) Cationic As stated earlier, the presence of a cationic polymer can potentiate the benefit of the hair growth promoter by improving its delivery to the hair and scalp. Examples of preferred cationic polymers include:
Guar Hydroxypropyltrimonium chloride
Quaternium-19
Quaternium-23
Quaternium-40
Quaternium-57
Poly(dipropyldiallylammonium chloride)
Poly(methyl-γ-propaniodiallylammonium chloride)
Poly(diallylpiperidinium chloride)
Poly(vinyl pyridinium chloride)
Quaternised poly (vinyl alcohol)
Quaternised poly (dimethylaminoethylmethacrylate); and mixtures thereof The amount of activity enhancer, when employed in accordance with the invention, will normally be from 0.1 to 50%, preferably from 0.5 to 25% and most preferably from 0.5 to 10% by weight of the composition.

Other Hair Growth Promoter Adjuncts

The composition according to the invention can also contain adjuncts other than those already mentioned, depending on the form of the intended product. It is, for example, possible to include antiseptics, preservatives, antioxidants, emulsifiers and colouring agents, pearlescers, foam boosters, conditioning agents (such as cationic surfactants, cationic polymers and silicones) and agents such as PFPE (perfluoropolyethylene) for improving hair gloss, which can improve the stability and consumer appeal of the composition.

The composition according to the invention can also be employed as a vehicle for a wide variety of cosmetically or pharmaceutically active ingredients, particularly ingredients which have some beneficial effect other than the promotion of hair growth when applied to the skin.

Surfactants

The composition for use in the method according to the invention can be formulated as a shampoo and will then accordingly comprise one or more surfactants which are cosmetically acceptable and suitable for topical application to the hair. Examples of suitable shampoo surfactants are now given.

Anionic Surfactant

The composition of the invention can comprise an anionic surfactant which is preferably chosen from alkyl sulphate, alkyl ether sulphate, alkyl sulphonate, alkyl aryl sulphonate, olefin sulphonate, acyl sarcosinate, acyl tauride, acyl isethionate, nonoalkyl sulphosuccinate, dialkylsulphosuccinate, acryl lactylate, acylated α-amino acid, allky carboxylate, monoalkyl phosphate and dialkyl phosphate.

Specific examples of anionic surfactants include:
alkyl sulphates, such as sodium lauryl sulphate [eg. EMPICOL CX available from Albright & Wilson], and triethanolaminde lauryl sulphate [eg. EMPICOL TL40/T, available from Albright & Wilson].
alkylether sulphates, such as sodium lauryl ether sulphate [eg. EMPICOL ESB70, available from Albright & Wilson].
alkyl sulphonates, such as sodium alkane ($C_{13-18}$) sulphonate [eg. HOSTAPUR SAS 30, available from Hoechst].
alkylaryl sulphonates, such as sodium alkyl benzene sulphonate [eg. TEEPOL CM44, available from Shell].
olefin sulphonates, such as sodium olefin sulphonate ($C_{5-18}$) [eg. HOSTAPUR OS, available from Hoechst].
acyl sarcosinates, having the structure: (51)

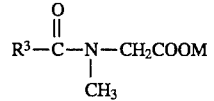

where $R^3$ is chosen from $C_{6-14}$ alkyl, and M is a counterion chosen from alkali metals, ammonium and substituted ammonium such as alkanolammonium.

An example of an acyl sarcosinate having the structure (51), is sodium laurly sarcosinate [eg. HAMPOSYL L-95, available from Grace].

acyl tautides, having the structure (52):

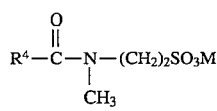

where $R^4$ is chosen from $C_{8-18}$ alkyl

An example of an acyl tauride having the structure (52) is coconut methyl taurine leg. FENOPEN TC 42, available from GAF].

acyl isethionates, having the structure (53):

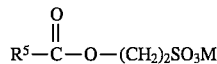

where $R^5$ is chosen from $C_{8-18}$ alkyl.

An example of an acyl isethionate having the structure (53) is sodium acyl isethionate [eg. JORDAPON C1, available from Jordon].

monoalkyl sulphosuccinates, having the structure (54):

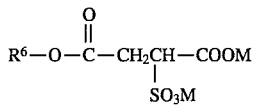

where $R^6$ is chosen from $C_{10-20}$ alkyl.

Examples of monoalkyl sulphosuccinates having the structure (54) include:

sodium lauryl sulphosuccinate [eg. EMPICOL SLL, available from Albright & Wilson].

magnesium alkyl sulphosuccinate [eg. ELFANOL 616 Mg, available from AKZO].

sodium lauryl ethoxysulphosuccinate [eg. EMPICOL SDD, available from Albright & Wilson].

coconut monoethanolamide ethoxysulphosuccinate [eg. EMPICOL SGG].

disodium lauryl polyglycolether sulphosuccinate [eg. SURTAGENE S30, available from CHEM-Y].

polyethyleneglycol sulphosuccinate [eg. REWOPOL SBFA 30, available from REWO].

dialkyl sulphosuccinates, having the structure (55):

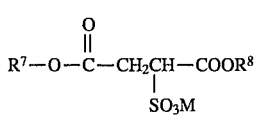

where $R^7$ and $R^8$ are the same or different, and are chosen from $C_{6-14}$ alkyl.

An example of a dialkyl sulphosuccinate having the structure (55) is sodium dilauryl sulphosuccinate [eg. EMCOL 4500, available from Witco].

acyl lactylates, having the structure (56):

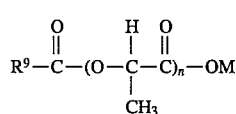

where $R_9$ is chosen from $C_{6-16}$ alkyl, and n is 1 or 2.

An example of an acyl lactylate having the structure (6) is decanoyl lactylate [eg. PATIONIC 122a, available from Patterson, CJ].

acylated α-amino acids, such as sodium lauroyl glutamate eg. ACYLGLUTAMATE LS-11, available from Ajinomoto Co. Inc].

ethyl carboxlates, such as alkyl $C_{12-14}O(EO)_4OCH_2CO_2Na$ [eg. AKYPO RLM 38, available from Akzo].

monoalkyl phosphates and dialkyl phosphates, such as dioctyl phosphate.

Amphoteric surfactant

The shampoo compositions of the invention also comprise amphoteric surfactant. Suitable amphoteric surfactants are derivatives of aliphatic quaternary ammonium, phosphonium and sulphonium compounds, wherein the aliphatic radicals contain from 8 to 18 carbon atoms, and may be straight chain or branched, and further contain an anionic water-solubilising group, such as carboxyl, sulphonate, sulphate, phosphate or phosphonate.

Preferred amphoteric surfactants include:

Alkyl betaines, having the structure (57):

where $R^1$ is $C_{1-16}$ alkyl.

An example of an alkyl betaine having the structure (7) is lauryldimethyl betaine [eg. EMPIGEN BB, available from Albright & Wilson].

Alkylamidopropyl betines, having the structure (58):

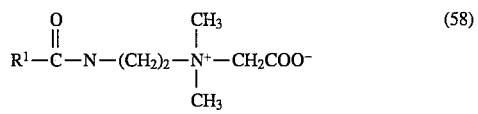

An example of an alkylamidopropyl betaine having the structure (58) is cocamidopropy betaine [eg. TEGOBETAIN L7, available from Goldschmidt).

Alkylamphoglycinates or Alkylamphopropionates having the structure (59):

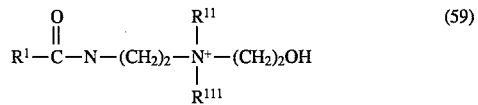

where $R^{11}$ is chosen from H, $CH_2COO^-$ and $(CH_2)_2COO^-$, and $R^{111}$ is chosen from $CH_2COO^-$ and $(CH_2)_2COO^-$ Suitable examples of compounds (59) are cocoamphoglycinate (available from GAF), and cocoamphopropionate.

Sultaines, having the structure (60):

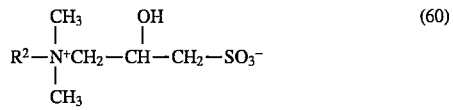

where $R^2$ is chosen from $C_{12-16}$ alkyl alkylamido groups.

An example of a sultaine having the structure (60) is cocamidopropylhydroxysultaine [eg. CYCLOTERIC BET-CS, available from Alcolac).

The most preferred amphoteric surfactant are lauryl dimethyl betaine and cocamidopropyl betaine.

Such amphoteric surfactants can contribute to the foaming of the shampoo of the invention, while ameliorating the harshness of the anionic surfactant.

Nonionic surfactant

The shampoo composition of the invention can also comprise alkoxylated or glycosidic nonionic surfactant having an HLB of 8 or more. Above this value nonionics generally form clear isotropic solutions in combination with the other surfactants in the ranges defined above. Preferred nonionic surfactants are polyoxyethylene alkyl esters and polyoxyethylene alkyl ethers and alkyl polyglycosides.

A suitable example of a polyoxyethylene alkyl ester is that having the CTFA designation Polysorbate 80 which is a mixture of oleate esters of sorbitol and sorbitol anhydrides, condensed with approximately 20 moles of ethylene oxide. Also suitable is Polysorbate 20 which is a mixture of laurate esters or sorbitol and sorbitol anhydrides condensed with approximately 20 moles of ethylene oxide.

Polysorbate 80 and Polysorbate 20 are available commercially as TWEEN 80 and TWEEN 20 respectively, from ICI Americas.

Also suitable for use in the compositions of the invention is the polyethylene glycol ether of $C_{9-11}$ alcohol with an average of 8 ethoxy units, which is available commerically as NONIDET LE-8T or as SYNPERONIC 91-8T, and the polyethylene glycol ether of $C_{12-15}$ alcohol with an average of 9 ethoxy units which is available commerically as DOBANOL 25-9.

Particularly useful alkyl polyglycosides include the glycosides of glucose or glucose oligomers where the alkyl chain can be $C_{8-16}$ and the average number of glucose units is 1 to 2. A suitable example is ORAMIX NS 10 which is the glucoside of $C_{10-12}$ fatty alcohol with an average of about 1.5 glucose units.

The amount of surfactant that can be present in the composition accordingly to the invention is up to 30%, preferably from 1 to 20% by weight of the composition.

Preservation of the Composition

The composition according to the invention is preferably preserved in such a manner that it will enjoy an extended shelf life following manufacture and prior to sale and use. Ideally the composition will have an indefinite shelf life.

It is accordingly apparent that the hair growth promoter is likely to be prone to attack by bacteria, moulds and fungi and other microbial influences, particularly at pH values near that of the skin that characterise the preferred composition. The shelf-life of the composition can therefore be unacceptably short due to the biodegradation of the hair growth promoter unless steps are taken to preserve the composition.

In order to be preserved, the composition should preferably be free, or substantially free, from viable microbial contaminants that are capable of resulting in microbial spoilage of the composition, and/or biodegradation of the hair growth promoter prior to topical application of the composition to mammalian skin or hair. It is to be understood, however, that the invention is also concerned with compositions, as herein defined, which may contain viable but dormant microorganisms, such as bacterial spores, provided that the conditions of preservation do not result in substantial proliferation of the microorganisms prior to use of the composition.

Examples of methods that can be employed to achieve preservation of the composition, includes the following:
(i) Sterilisation The composition according to the invention can be preserved by sterilisation to remove or kill substantially all viable microbial contaminants. This can be achieved for example by irradiation using a lethal dose of gamma rays, by heat sterilisation or by ultrafiltration using techniques that are well established in the pharmaceutical industry.
(ii) Chemical Preservative The composition according to the invention can also be preserved by including in it a chemical preservative which functions to prevent the growth of or kill bacteria, fungi or other microorganisms.

Examples of chemical preservatives include ethanol, benzoic acid, sodium benzoate, sorbic acid, potassium sorbate, sodium propionate and the methyl, ethyl, propyl and butyl esters of p-hydroxybenzoic acid. The amount of chemical preservative that can be incorporated in the composition according to the invention will generally be from 0.05 to 5%, preferably from 0.1 to 2% by weight, the amount chosen being sufficient to arrest microbial proliferation.
(iii) Water activity depressants The composition according to the invention can also be preserved by the inclusion of a water activity depressant such as glycerol, propylene glycol, sorbitol, sugars and salts, for examples alkali metal halides, sulphates and carboxylates. When employing a water activity depressant, sufficient should be incorporated in the composition according to the invention to reduce the water activity ($\alpha_w$) from 1 to <0.9, preferably to < 0.85 and most preferably < 0.8, the lowest of these values being that at which yeasts, moulds and fungi will not proliferate.

pH

The hair growth promoter may be susceptable to hydrolysis, particularly when the pH value of the composition is alkaline. It is accordingly preferred that the composition, when aqueous, should have an acid pH value. The preferred pH value of the composition, when aqueous, is from 2 to <7, ideally from 4 to 6.5.

Process

The invention also provides a process for the preparation of a composition suitable for topical application to mammalian skin or hair which comprises mixing a hair growth promoter as herein defined, with a suitable vehicle to provide a composition according to the invention, in which the hair growth promoter forms from 0.0001 to 99% by weight of the composition.

Product Form and Container

The compositions of the invention can be formulated as liquids, for example as a lotion, shampoo, conditioner, milk or cream for use in conjunction with an applicator such as a roll-ball applicator, or a spray device such as an aerosol can containing propellant, or a container fitted with a pump to dispense the liquid product. Alternatively, the compositions of the invention can be solid or semi-solid, for example sticks, creams or gels, for use in conjunction with a suitable applicator or simply a tube, bottle or lidded jar, or as a liquid-impregnated fabric, such as a tissue wipe.

The invention accordingly also provides a closed container containing a composition as herein defined.

Use of the Hair Growth Promoter

The invention also provides for the use of hair growth promoter as herein defined, for topical application to mammalian skin or hair for inducing, maintaining or increasing hair growth.

The compositions according to the invention are primarily intended for topical application to the scalp of the human subject, particularly where the head is already bald or balding, in order to convert vellus hair to growth as terminal hair, or to increase the rate of growth of terminal hair. The compositions can also be applied profilactically to the hair and hence the scalp to reduce or prevent the onset of baldness.

The amount of the composition and the frequency of application to the hair and/or scalp can vary widely, depending on personal needs, but it is suggested as an example that topical application of from 0.1 to 5 g daily containing from 0.00001 to 1 g of a selected chemical inhibitor over the period of at least six months will in most cases result in an improvement in hair growth.

EVALUATION OF EFFICACY OF THE HAIR GROWTH PROMOTERS USING THE IN VITRO HAIR FOLLICLE GROWTH TEST

The effect of compounds on hair growth was assessed using an in vitro test which measures the elongation of isolated human hair follicles in a culture medium.

Isolation of the Hair Follicle from Skin

This test includes the important step of isolating hair follicles having an undamaged hair bulb from human skin, for example, facelift skin, by microdissection.

The critical step of separating the hair follicle with intact undamaged hair bulb from the subcutaneous fatty tissue in which it is situated accordingly involves severing the hair shaft of the follicle at a point below the epidermis of skin surface, so as to leave the hair bulb intact and undamaged while still bearing a portion of the hair shaft.

Preferably, the hair shaft of the follicle is severed at the dermal-subcutaneous fat interface.

Any suitable cutting instrument can be employed to sever the hair shaft in this manner, but a keratotome or a scalpel are preferred.

The hair bulb with a hair Shaft stump attached is then isolated from the skin by mechanically separating the hair from loosely adhering subcutaneous fat which normally surrounds the hair bulb. This is achieved after the dermis or upper layer of the skin has been separated and removed, to avoid damaging the hair bulb as it is pulled away.

The hair bulb together with hair shaft stump attached, is then transferred in an otherwise undamaged and fully functioning, viable state to a nutrient medium.

Culture of the Isolated Hair Follicle

The hair follicles isolated by the technique described herein are transferred to a suitable culture medium for subsequent testing of substances that can then influence their future development.

The procedure now to be described represents a preferred method of culture and testing of hair growth.

In accordance with the preferred method of culture, isolated hair follicles, obtained from facelift skin from a 61 year old female, are maintained in 1 ml of Williams E medium, either with or without a test hair growth substance, supplemented with antibodies (Penicillin and Streptomyein), Insulin (10 ng/ml) and Hydrocortisone (10 ng/ml). The medium was incubated at 37° C. in an atmosphere of 5% $CO_2$+ 95% air in individual wells of a 24 multiwell dish (Corning), which permits detailed measurements to be made of the length of individual hair follicles. The medium was refreshed once during the experiment after 4 days.

Williams E medium is available from FLOW Laboratory under Catalogue No. 12-502. The formula of Williams E medium is described by Williams GM, et al., in Experimental Cell Research 69 (1971) on page 106.

Daily growth rate and cumulative growth for each follicle were calculated by measuring the change in length of the follicles each day and from this the average of all the follicles was calculated.

Evaluation of Results

The response of an isolated hair follicle to a test substance, can accordingly be assessed by measuring the increase in length, if any, in the presence of a test substance against a control.

The in vitro method described herein was used to assess the effect of two 'fuels' (hair growth promoters), namely α-alanylglutamine and glutamine on hair growth.

The results obtained are summarised in the following Table.

| Hair growth promoter in Williams E medium & glucose | Amount of hair grown in one week | Average daily rate of growth of hair over one week |
| --- | --- | --- |
| Ala-Gln dipeptide 2 mM | 2.22 mm | 0.308 mm/d |
| Glutamine 2 mM | 2.02 mm | 0.277 mm/d |
| Control (no Glutamine) | 1.32 mm | 0.162 mm/d |

* these results in each case are the mean of 5 different follicles taken from 5 different human subjects (25 follicles in total).

The results summarised above indicated the significant increase in hair growth, as compared with the control, that can be achieved with either glutamine or α-alanylglutamine as hair growth promoters. Clearly, alanylglutamine is as potent as glutamine in this respect with fresh stock materials. After 3 months storage at 20° C., the potency of glutamine had diminished significantly while that of the peptide, α-alanylglutamine retained its potency undiminished.

These results are also illustrated in FIG. 1 in which the ordinate depicts the hair growth (mm) and the abscissa depicts cumulative time (hours).

EXAMPLES

The invention is illustrated by the following examples.

Example 1

This Example illustrates a lotion according to the invention which is suitable for topical application to the scalp in order to promote hair growth.

The lotion has the following formulation:

|  | % w/w |
| --- | --- |
| α-alanylglutamine (2) | 1 |
| ethanol | 99 |
| perfume | q.s. |

Example 2

This Example illustrates a hair tonic which is suitable for application to hair or scalp.

The hair tonic has the following formulation:

|  | % w/w |
| --- | --- |
| nonanoyl glutamine (22) | 2 |
| ethanol | 49 |
| water | 49 |
| perfume | q.s. |

Example 3

This Example also illustrates a lotion which is suitable for topical application to the scalp.

The lotion has the following formulation:

|  | % w/w |
|---|---|
| Promoter No. (3) | 3 |
| propan-2-ol | 10 |
| ethanol | 87 |
| perfume | q.s. |

Example 4

This Example also illustrates a hair tonic which is suitable for application to hair or scalp.

The hair tonic has the following formulation:

|  | % w/w |
|---|---|
| Promoter No. (7) | 3 |
| ethanol | 40 |
| water | 57 |
| perfume | q.s. |

Examples 5 to 8

The following formulations represent lotions which can be used topically in the treatment of bald or balding male or female heads.

|  | % w/w | | | |
|---|---|---|---|---|
|  | 5 | 6 | 7 | 8 |
| Hydroxyethyl cellulose | 0.4 | — | 0.4 | — |
| Absolute ethanol | 25 | 25 | 25 | 25 |
| Propane-1,2-diol | — | — | 38.4 | 38.4 |
| Butane-1,3-diol | 38.4 | 38.8 | — | — |
| Paramethyl benzoate | 0.2 | 0.2 | 0.2 | 0.2 |
| Promoter No. (12) | 5 | — | — | — |
| Promoter No. (13) | — | 4 | — | — |
| Promoter No. (17) | — | — | 3 | — |
| N-acetyl proline | 0.6 | 0.6 | 0.6 | 0.6 |
| Perfume | 1 | 1 | 1 | 1 |
| Water | to 100 | 100 | 100 | 100 |

Examples 9 to 12

The following formulations represent creams which can be used in the treatment of baldness.

|  | % w/w | | | |
|---|---|---|---|---|
|  | 9 | 10 | 11 | 12 |
| Cetyl alcohol polyoxyethylene (10) | 4 | 4 | 4 | 4 |
| Cetyl alcohol | 4 | 4 | 4 | 4 |
| Mineral oil | 4 | 2 | — | — |
| Paraffin wax | — | 2 | 4 | — |
| Promoter No. 21 | — | — | — | 4 |
| Promoter No. 22 | 2 | — | — | — |
| Promoter No. 25 | — | 2 | — | — |
| Promoter No. 28 | — | — | 2 | — |
| minoxidil | 0.5 | 0.5 | 0.5 | 0.5 |
| Triethanolamine | 0.75 | 0.75 | 0.75 | 0.75 |
| Butane-1,3-diol | 3 | 3 | 3 | 3 |
| Xanthan gum | 0.3 | 0.3 | 0.3 | 0.3 |

-continued

|  | % w/w | | | |
|---|---|---|---|---|
|  | 9 | 10 | 11 | 12 |
| Preservative | 0.4 | 0.4 | 0.4 | 0.4 |
| Perfume | q.s. | q.s. | q.s. | q.s. |
| Water | to 100 | 100 | 100 | 100 |

Example 13

This Example illustrates a water-in-oil high internal phase emulsion containing an amine according to the invention.

The emulsion consisted of 10% by volume oily phase and 90% by weight aqueous phase.

The oily phase and the aqueous phase had the following constitution: keel

|  | % w/w |
|---|---|
| Oily phase |  |
| Sorbitan monooleate | 20 |
| Quaternium-18 hectorite | 5 |
| Liquid paraffin | 75 |
| Aqueous phase |  |
| Promoter No. 33 | 1 |
| Xanthan gum | 1 |
| Preservative | 0.3 |
| Perfume | q.s. |
| Sodium chloride (1% w/w solution) | to 100 |

The emulsion was prepared by taking 10 parts by volume of the oily phase and to it adding slowly with stirring 90 parts by volume of the aqueous phase.

The high internal phase water-in-oil emulsion so formed can be applied topically to the scalp, to improve hair growth and regrowth.

The following examples 14 to 18 illustrate shampoos for use in washing the hair and scalp, and for promoting hair growth on the scalp.

Example 14

|  | % w/w |
|---|---|
| Sodium lauryl ether sulphate (2 EO) [21% AD] | 41.4 |
| Lauryl dimethylamino acetic acid betaine: [30% AD] | 4 |
| Coconut fatty acid diethanolamine | 1.5 |
| Oleyl triethoxy phosphate (BRIPHOS 03D) | 1 |
| Polyglycol-polyamine condensation resin (POLYQUART H) [50% active] | 1.5 |
| Preservative, colouring matter, salt | 0.58 |
| Promoter No. 29 | 10 |
| Perfume | q.s. |
| Water | to 100 |

Example 15

|  | % w/w |
|---|---|
| Sodium lauryl ether sulphate (2 EO) [100% AD] | 12 |
| POLYMER JR400 | 2.5 |
| BRIPHOS 03D | 2.5 |

|  | % w/w |
|---|---|
| Promoter No. 30 | 15 |
| Magnesium Sulphate | 5 |
| Perfume | q.s. |
| Water | to 100 |

Example 16

This Example also illustrates a lotion which is suitable for topical application to the scalp.

The lotion has the following formulation:

|  | % w/w |
|---|---|
| Promoter No. 35 | 5 |
| minoxidil | 1 |
| propan-2-ol | 10 |
| ethanol | 84 |

Examples 17

This example illustrates a powder composition according to the invention which can be applied topically to the scalp.

|  | % w/w |
|---|---|
| Chemically modified starch | 5 |
| Chemically modified cellulose | — |
| Boric acid | 10 |
| Zinc oxide | 5 |
| Promoter No. 36 | 3 |
| Minoxidil | 5 |
| Perfume | q.s. |
| Chalk | 10 |
| Talc | to 100 |

Example 18

The following example illustrates a lotion according to the invention which can be applied topically to the scalp to prevent hair loss and stimulate hair regrowth.

|  | % w/w |
|---|---|
| nonanoyl glutamine (22) | 7 |
| glucaro-1,4-lactone | 2 |
| ethanol | 16 |
| citric acid | 1.05 |
| water | to 100 | pH adjusted to 4.2 with sodium hydroxide

Examples 19 & 20

These examples illustrate hair tonics which are suitable for application to the hair and scalp.

The hair tonics had the following formulation:

|  | % w/w | |
|---|---|---|
|  | 19 | 20 |
| α-alanoyl glutamine (2) | — | 2 |
| Promoter No (3) | 2 | — |
| glucaro-1,5-lactam | 3 | 3 |

|  | % w/w | |
|---|---|---|
|  | 19 | 20 |
| ethanol | 50 | 50 |
| water | 45 | 45 |

Example 21

This example illustrates a shampoo which is suitable for topical application to hair in order to cleanse it, at the same time delivering an inhibitor to the scalp to enhance hair growth or regrowth.

The shampoo had the following formulation:

|  | % w/w |
|---|---|
| Triethanolamine lauryl sulphate | 16.8 |
| Coconut diethanolamide | 3.0 |
| Hydroxypropylmethyl-cellulose (1) | 0.25 |
| Corn syrup (80% solids) (2) | 20.5 |
| Dimethylpolysiloxane (3) | 1.0 |
| Cationic cellulose (4) | 0.5 |
| Ethyl alcohol (SDA 40) | 9.0 |
| Vinyl carboxy polymer (5) | 0.75 |
| Promoter No. 41 | 8 |
| Perfume, colour, preservative | q.s. |
| Water | to 100 |

Acid or base to pH: 6.5
1— Methocel E4M (Dow Chemical)
2—42 Dextrose equivalent (Staley 1300)
3—60,000 centistokes (Viscasil, GEC)
4—Polymer JR 400
5—Carbopol 941 (BF Goodrich)

Example 22

This example illustrates a shampoo in accordance with the invention.

The shampoo had the following formulation:

|  | % w/w |
|---|---|
| Sodium lauryl ether sulphate (3EO) | 10 |
| Pearlising agent | 4 |
| Betaine | 2 |
| Cationic polymer | 0.2 |
| 1-α-alanylglutamine | 0.5 |
| minor ingredients | 4 |
| water | to 100 | pH value 6 to 7
viscosity: 3500 to 4000 cps (Brookfield Spindle No. 3 at 10 rpm 25° C.)

Example 23

This example illustrates a shampoo in accordance with this invention.

The shampoo had the following formulation:

|  | % w/w |
|---|---|
| Sodium lauryl ether sulphate [3EO] (70% AD) | 20 |
| Pearlising agent | 2 |
| Betaine | 6 |
| Butyl glutamine | 1 |

| | % w/w |
|---|---|
| Silicone emulsion | 1 |
| Cationic polymer | 0.1 |
| D-panthenol | 0.4 |
| Carbopol | 0.4 |
| Sodium chloride | 2.5 |
| Minor ingredients | 8.5 |
| water | to 100 | pH value 6.5 viscosity: 5000 cps (Brookfield Spindle No. 3 at 10 rpm, 25° C.)

We claim:

1. A method for maintaining or increasing hair growth by topically applying to mammalian hair a composition comprising:
   i. from 0.001 to 99% by weight of a hair growth promoter which is a glutamine dipeptide; and
   (ii) from 1 to 99.99% by weight of a cosmetically acceptable vehicle for the hair growth promoter.

2. A method according to claim 1 wherein the hair growth promoter is α-alanylglutamine or its cosmetically acceptable salt.

3. A method according to claim 1 in which the hair growth promoter forms from 0.01 to 20% by weight of the composition.

4. A method according to claim 1 which further comprises an activity enhancer.

5. A method according to claim 4 in which the activity enhancer is a hair growth stimulant.

6. A method according to claim 5 in which the hair growth stimulant is minoxidil.

7. A method according to claim 4 in which the activity enhancer is a penetration enhancer.

8. A method according to claim 4 in which the activity enhancer is a cationic polymer.

9. A method according to claim 1 which further comprises a surface active agent.

10. A method according to claim 1 which has a pH value in a range from 2 to less than 7.

11. A method according to claim 1 which is a shampoo or hair conditioner.

12. A method according to claim 1 wherein the hair growth promoter is selected from the group consisting of glycinylglutamine, glutaminylglutamine and cosmetically acceptable salts thereof.

* * * * *